United States Patent [19]
Nakanishi

[11] Patent Number: 5,911,579
[45] Date of Patent: Jun. 15, 1999

[54] DENTAL HANDPIECE WITH BAFFLE FOR STABILIZING ROLLING BEARING CAGE

[75] Inventor: Takasuke Nakanishi, Kanuma, Japan

[73] Assignee: Nakanishi, Inc., Tochigi-ken, Japan

[21] Appl. No.: 09/092,813

[22] Filed: Jun. 5, 1998

[30] Foreign Application Priority Data

Jun. 9, 1997 [JP] Japan ................................ 9-150926

[51] Int. Cl.⁶ ...................................... A61C 1/05
[52] U.S. Cl. ............................................ 433/132
[58] Field of Search ................... 433/114, 115, 433/116, 126, 132

[56] References Cited

U.S. PATENT DOCUMENTS

| | | | |
|---|---|---|---|
| 4,219,330 | 8/1980 | Jaremus | 433/132 X |
| 4,225,308 | 9/1980 | Lohn | 433/132 |
| 4,318,695 | 3/1982 | Lieb et al. | 433/132 |
| 4,326,846 | 4/1982 | Sugai et al | 433/132 |
| 4,533,324 | 8/1985 | Nakanishi | 433/132 |
| 4,941,828 | 7/1990 | Kimura | 433/132 |
| 5,423,678 | 6/1995 | Nakanishi | 433/132 X |
| 5,733,120 | 3/1998 | Yao et al. | 433/132 |

*Primary Examiner*—Nicholas D. Lucchesi
*Attorney, Agent, or Firm*—Malcolm B. Wittenberg

[57] ABSTRACT

A dental handpiece is disclosed which includes:

- a head housing provided at a distal end of the dental handpiece,
- a burr sleeve for unrotatably holding a dental treatment tool,
- upper and lower ball bearings for rotatably supporting the burr sleeve, each of the upper and lower ball bearings having an inner ring, an outer ring, and a plurality of balls between the inner and outer rings,
- a rotor disposed between the upper and lower ball bearings and rotated by a compressed air for rotatively driving the burr sleeve, the rotor defining a rotation space within the head housing,
- a rolling bearing cage for supporting the plurality of balls at regular intervals in each of the upper and lower ball bearings, the cage having a side facing the rotor, and
- a baffle member disposed facing the side of the cage to define a first gap between the baffle member and the cage.

7 Claims, 4 Drawing Sheets

DENTAL HANDPIECE WITH BAFFLE FOR STABILIZING ROLLING BEARING CAGE

FIELD OF THE INVENTION

The present invention relates to a dental handpiece, and more specifically a dental handpiece provided with ball bearings wherein wearing of balls and a cage of ball bearings is minimized.

BACKGROUND ART

In conventional dental handpieces, in particular those provided with an air turbine as shown in FIG. 4 having rotor 16 which rotatively drives burr sleeve 13, the burr sleeve 13 is rotatably supported by upper and lower ball bearings 14, 15. In some types of ball bearings, a plurality of balls 14c, 15c between inner and outer rings 14a, 15a, 14b, 15b of the bearings are supported by rolling bearing cages 17, 18 at regular circumferential intervals.

In these types of ball bearings, however, the cages 17, 18 supporting the balls 14c, 15c are shaken up and down due to the rotation of the burr sleeve. Thus, the cages 17, 18 are kept in unstable contact with the balls 14c, 15c, which causes wearing and damaging of both the balls and the cages, as well as shaking and noise of the overall handpiece. In particular, if a rolling bearing cage of crown type having a plurality of pockets with an opening for supporting the balls therein is used, the area supporting the balls in the pockets is smaller near the openings than other portions, and thus wearing of the cage is localized near the openings, leading to premature termination of the service life of the cage. Although the cages are pressed axially outwardly to some extent by the air stream flowing between the inner and outer rings of the bearings, the cages are not kept in sufficiently stable contact with the balls in the bearings.

Some of the conventional dental handpieces are further provided with dust preventive members 21, 22 projecting from and rotating with the burr sleeve 13 for preventing debris, saliva, blood, or the like from entering the interior of the head housing 11. The dust preventive members define on their outer surfaces gaps A which communicate with the rotation space of the rotor 16 via the upper or lower ball bearings 14, 15 at one end, and with outside the head housing 11 at the other end. Rotation of the dust preventive members 21, 22 generates high pressure areas in the gaps between the rotation space of the rotor 16 and outside the head housing 11, to thereby remarkably block the air stream out of the head housing 11. Consequently, even when the rotation of the rotor is stopped to establish negative pressure in the head housing 11, debris, saliva, blood, or the like will not be sucked into the interior of the head housing 11.

However, blocking of the air stream out of the head housing 11 will cause reduced flow of the air stream between the inner and outer rings of the ball bearings 14, 15. Therefore, the axially outward pressure exerted on the cages 17, 18 becomes still less sufficient for stabilizing the cages 17, 18, compared to the former type of the handpiece without the dust preventive members, and thus the cages are kept in less stable contact with the balls.

DISCLOSURE OF THE INVENTION

The present invention is made to solve the above problems of the prior arts. Therefore, it is an object of the present invention to provide a dental handpiece wherein wearing of the balls and the rolling bearing cages in the ball bearings is minimized.

It is another object of the present invention to provide a dental handpiece wherein wearing of the balls and the rolling bearing cages in the ball bearings is minimized, while sucking of debris, saliva, blood, and the like into the head housing is prevented.

It is another object of the present invention to provide a dental handpiece which provides higher speed of rotation and greater torque of the rotor, while the above objects are achieved.

According to the present invention, there is provided a dental handpiece comprising:

- a head housing provided at a distal end of the dental handpiece,
- a burr sleeve for unrotatably holding a dental treatment tool,
- upper and lower ball bearings for rotatably supporting said burr sleeve, each of said upper and lower ball bearings having an inner ring, an outer ring, and a plurality of balls between said inner and outer rings,
- a rotor disposed between said upper and lower ball bearings and rotated by a compressed air for rotatively driving said burr sleeve, said rotor defining a rotation space within the head housing,
- a rolling bearing cage for supporting said plurality of balls at regular intervals in each of said upper and lower ball bearings, said cage having a side facing the rotor, and
- a baffle member disposed facing said side of the cage to define a first gap between said baffle member and the cage.

PREFERRED EMBODIMENTS OF THE INVENTION

The present invention will now be explained with reference to the drawings depicting preferred embodiments of the present invention, but the present invention is not limited thereto.

Figure 1:
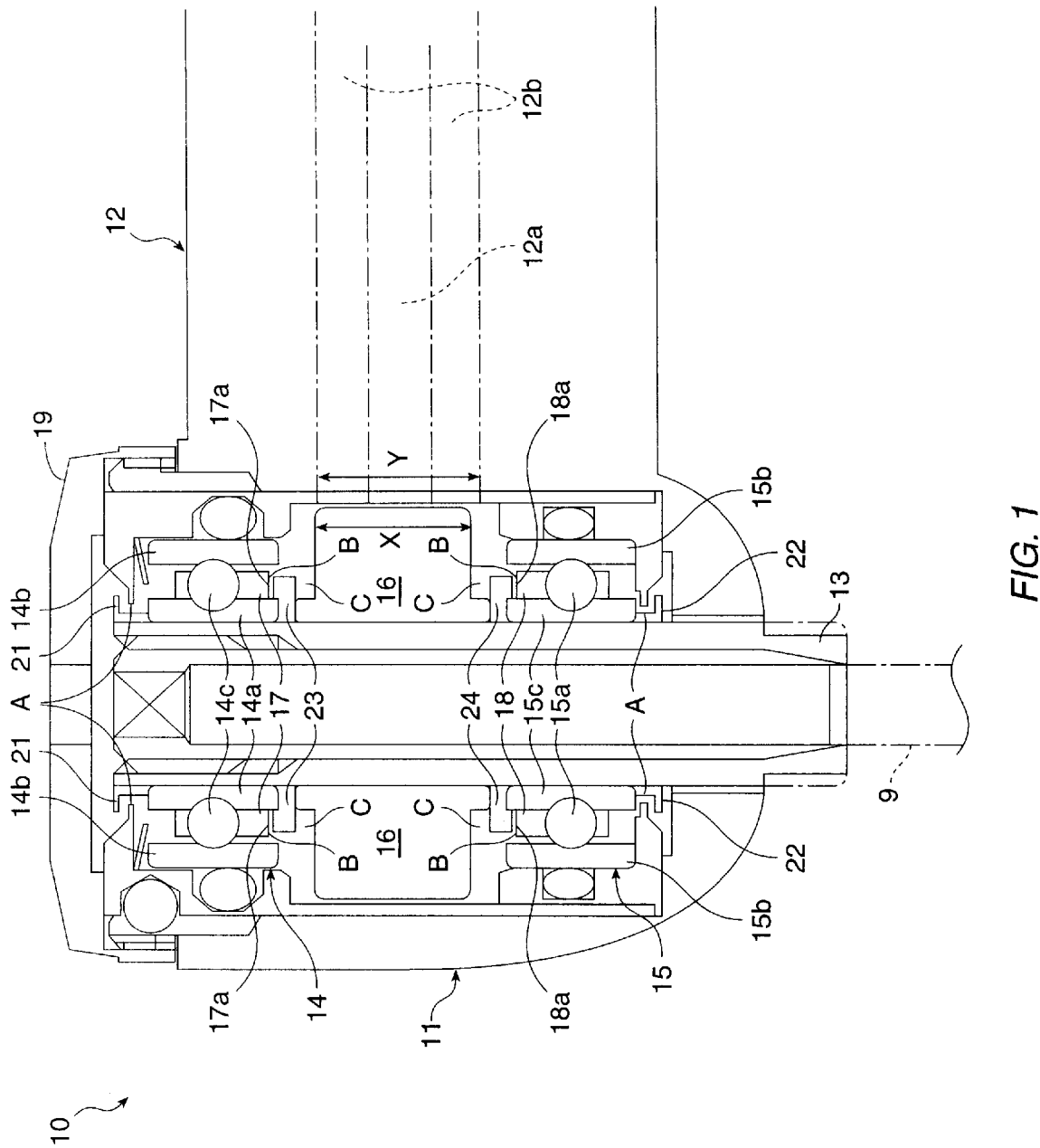
FIG. 1 is a schematic sectional view of an embodiment of a dental handpiece of the present invention.

FIG. 1 schematically shows a sectional view of dental handpiece 10 of the present invention. The dental handpiece 10 has head housing 11 which accommodates burr sleeve 13 for unrotatably holding dental treatment tool 9 therein, upper and lower ball bearings 14, 15 for rotatably supporting the burr sleeve 13, and rotor 16 secured to the burr sleeve 13 between the upper and lower bearings 14, 15 to rotatively driving the burr sleeve 13 and defining a rotation space in the head housing 11. The head housing 11 is mounted at the distal end of head housing jacket 12, which accommodates air supply passage 12a for supplying a compressed air to the rotor 16, and air discharge passage 12b for discharging the compressed air out of the head housing 11.

The air supply passage 12a has a port opened to the rotation space of the rotor 16 at its distal end, through which the compressed air is supplied to the rotor 16. The air discharge passage 12b has a port opened to the rotation space at its distal end, through which the compressed air having been used for rotating the rotor 16 is discharged out of the head housing 11. The diameter Y of the port of the discharge passage 12b measured in the axial direction of the burr sleeve 13 is substantially equal to the axial length X of the rotor 16.

The compressed air supplied via the air supply passage 12a through the port into the rotation space rotates the rotor 16 to rotatively drive the burr sleeve 13, and then is discharged via the air discharge passage 12b through the port out of the head housing 11.

The upper ball bearing 14 has inner ring 14a, outer ring 14b, and a plurality of balls 14c therebetween. The balls 14c are supported by rolling bearing cage 17 at regular circumferential intervals. Similarly, the lower ball bearing 15 has inner ring 15a, outer ring 15b, and a plurality of balls 15c therebetween. The balls 15c are supported by rolling bearing cage 18 at regular circumferential intervals.

Figure 2A:
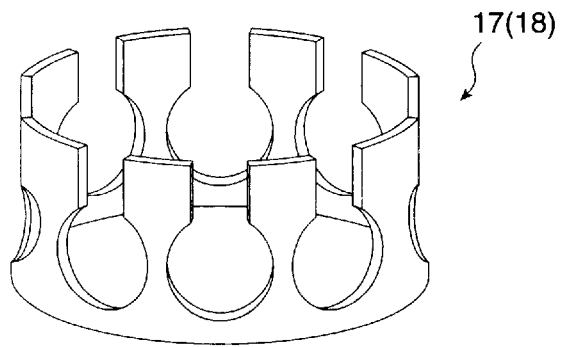
FIGS. 2(a)–(d) are schematic perspective views of examples of a rolling bearing cage used in the dental handpiece of the present invention.

The rolling bearing cages 17, 18 in the embodiment shown in FIG. 1 are of crown type as shown in FIG. 2(a) Each of the cages 17, 18 has generally cylindrical configuration, and provided with a plurality of pockets for rotatably receiving the balls 14c, 15c therein. Each pocket has an opening opened to one end of the cage. The cages 17, 18 are symmetrically disposed in the upper and lower bearings 14, 15, respectively, so that the openings of the pockets are oriented in the opposite directions, i.e. oriented axially inwardly, facing each other.

Figure 2B:
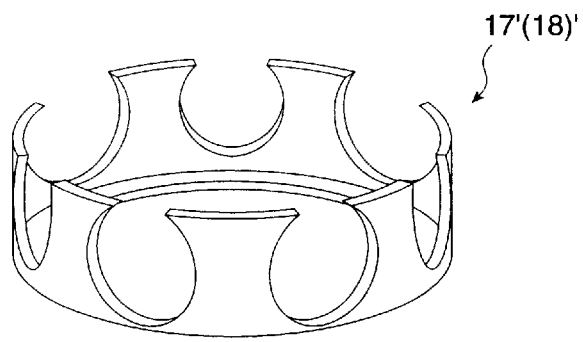
Figure 2C:
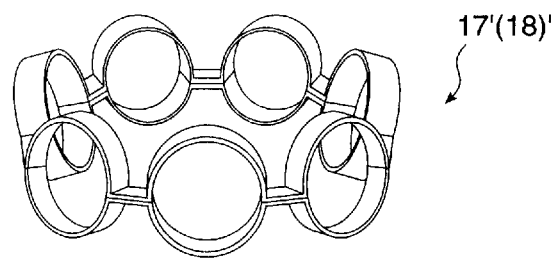
Figure 2D:
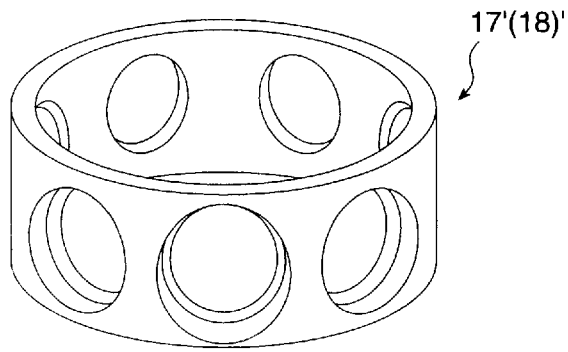

Although the cages 17, 18 of crown type are specifically described above, cages of other configurations, such as cages 17', 18' shown in FIGS. 2(b)–(d) may as well be used as the rolling bearing cages in the present handpiece.

Referring back to FIG. 1, the dental handpiece 10 may be provided with dust preventive members 21, 22 on the outer surface of the burr sleeve 13 at locations axially outwardly of and adjacent to the upper and lower bearings 14, 15, respectively. Each of the dust preventive members 21, 22 has an axially extending portion secured to the outer surface of the burr sleeve 13, and a radial portion extending radially outwardly from the burr sleeve 13.

The outer surface of the dust preventive member 21 defines gap A which communicates with the upper bearing 14 at one end, and outside of the head housing 11 via a gap between the head housing 11 and head cap 19 mounted on top of the housing 11 at the other end. Similarly, the outer surface of the dust preventive member 22 defines gap A which communicates with the lower bearing 15 at one end, and outside of the head housing 11 via a gap between the lower portion of the head housing 11 and the burr sleeve 13 at the other end.

When the dust preventive members 21, 22 rotate with the burr sleeve 13, high pressure areas are established in the gaps A at the location having the smallest width. These high pressure areas remarkably block the air stream out of the head housing 11 caused by the rotation of the rotor 16, so that even when the rotation of the rotor 16 is stopped to establish negative pressure in the head housing 11, debris, saliva, blood, or the like will not be sucked into the interior of the head housing 11 through the gaps A.

Although the dust preventive members 21, 22 are described as above, the configuration and the position of the dust preventive members are not particularly limited as long as the above effect is obtained.

Baffle 23 is disposed between the upper bearing 14 and the rotor 16 with the axially outer side of the baffle 23 facing to the axially inner side 17a of the rolling bearing cage 17. Similarly, baffle 24 is disposed between the lower bearing 15 and the rotor 16 with the axially outer side of the baffle 24 facing to the axially inner side 18a of the rolling bearing cage 18. The baffles 23, 24 are fixed on and rotated with the burr sleeve 13.

Figure 3A:
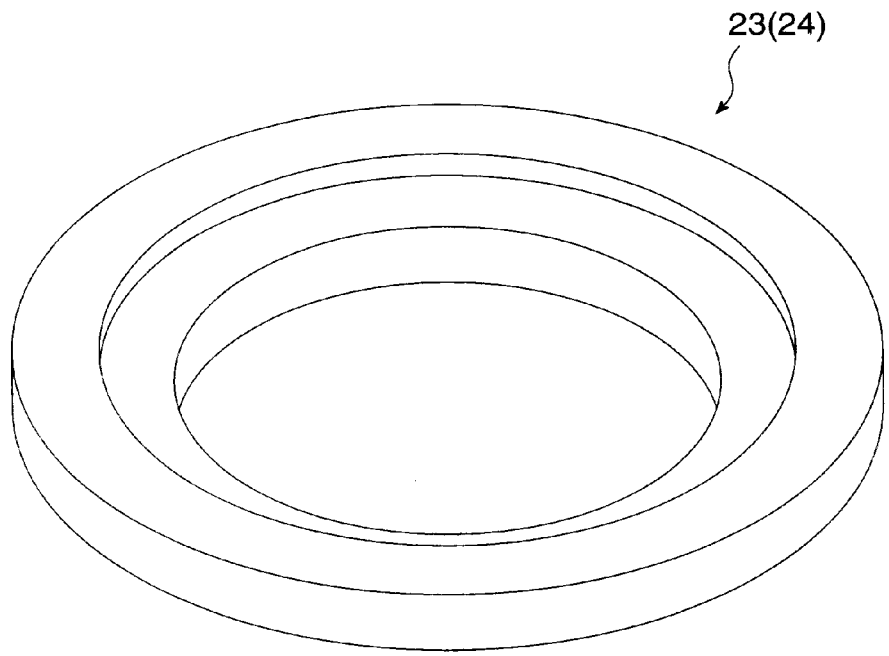
FIG. 3(a) is an enlarged view of an embodiment of a baffle with an annular step used in the dental handpiece of the present invention.

Each of the baffles 23, 24 is a generally annular disc, and has a raised annular step on one side at the peripheral portion of the disc as shown in FIG. 3(a). The step of the baffle 23 is arranged facing to the side 17a of the cage 17 to define gap B between axially outer side of the baffle 23 and the side 17a, whereas the step of the baffle 24 is arranged facing to the side 18a of the cage 18 to define gap B between the axially outer side of the baffle 24 and the side 18a.

The size of the gap B should be kept as small as possible, and is preferably about 0.2 mm to about 0.3 mm when the play between the balls 14c, 15c and the cages 17, 18 for allowing rotation of the balls are about 0.05 mm to about 0.2 mm.

The gaps B function to optimize the air stream between the inner and outer rings of the ball bearings 14, 15, to thereby stabilize the cages 17, 18 in respect to the balls 14c, 15c for preventing wearing of the cages 17, 18 and the balls 14c, 15c. This is because a layer of air is formed in the gaps B, which suppresses shaking of the cages 17, 18 to stabilize the rotation of the cages 17, 18.

The baffle 23 also defines gap C between the axially inner side of the baffle 23 and the rotor 16, whereas the baffle 24 defines gap C between the axially inner side of the baffle 24 and the rotor 16.

The gaps C function to receive a portion of the compressed air supplied to rotate the rotor 16, and promote the rotation of the rotor 16 upon discharging the air into the air discharge passage 12b, since the axial length X of the rotor 16 is substantially equal to the diameter Y of the port of the passage 12b. Accordingly, the rotation speed and the torque of the rotor 16 are improved.

Figure 3B:
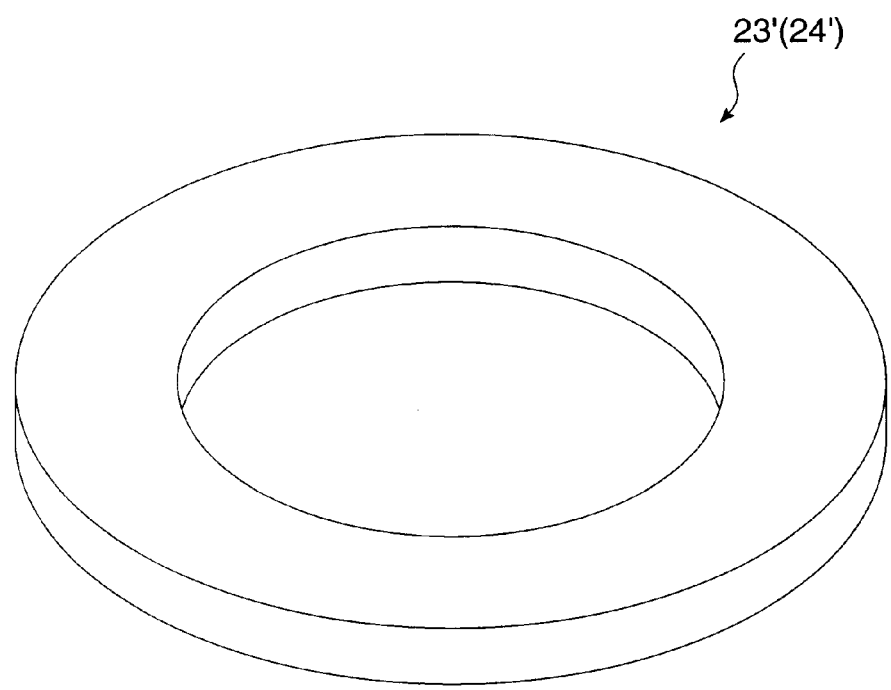
FIG. 3(b) is an enlarged view of another embodiment of a baffle without the annular step used in the dental handpiece of the present invention.
Figure 4:
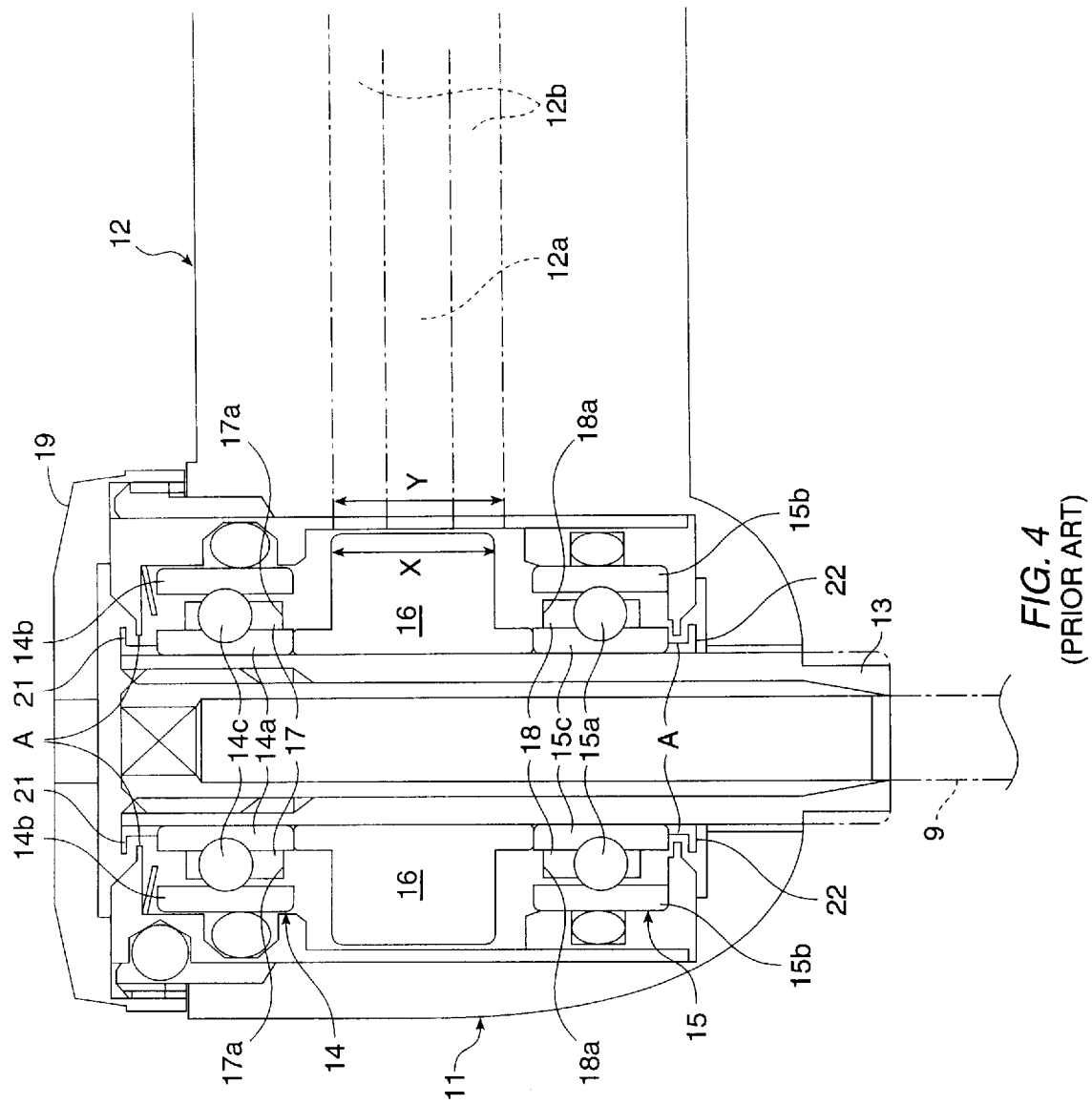
FIG. 4 is a schematic sectional view of a conventional dental handpiece having dust preventive members.

The configuration and the position of the baffles 23, 24 are not particularly limited as long as the above effects are obtained. For example, the baffles 23, 24 may be stationarily fixed on the inner surface of the head housing 11. Further, baffles of other configuration, such as baffles 23', 24' without a step as shown in FIG. 3(b) may as well be used in place of the baffles 23, 24.

In addition, the configuration of the gaps B is not particularly limited as long as a thin layer of air is formed between the cages 17, 18 and the baffles 23, 24 to suppress shaking of the cages 17, 18. The configuration of the gaps C is not particularly limited as long as the gap functions to promote the rotation of the rotor 16.

According to the present invention, a baffle member is provided facing each rolling bearing cage to define a gap between the baffle member and the cage. Therefore, the air streams flowing between the inner and outer rings of the ball bearings are optimized to stabilize the cages with respect to the bearing balls. Accordingly, wearing of the cages and the balls is minimized. In other words, a layer of air is formed between the baffles and the cages upon driving the handpiece to suppress shaking of the cages, thereby minimizing shaking and noise of the over all handpiece.

Further, the baffles may also be provided in a dental handpiece having dust preventive members. With this structure, the air streams flowing between the inner and outer rings of the ball bearings are optimized due to the gaps to stabilize the cages, while the air streams out of the head housing are remarkably blocked. Accordingly, wearing of the cages and the balls of the bearings is minimized, while debris, saliva, blood, and the like are prevented from being sucked into the interior of the head housing wherein a negative pressure is established upon stopping the rotation of the rotor.

In addition, since the baffles define another gaps between the baffles and the rotor, and the axial length of the rotor is substantially equal to the diameter of the port of the air discharge passage measured in the axial direction of the burr sleeve, a portion of the compressed air supplied to rotate the rotor enters the gaps, and promotes the rotation of the rotor upon exiting the gaps into the air discharge passage. Accordingly, the rotation speed and the torque of the rotor are improved.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece comprising a head housing provided at a distal end of the dental handpiece, a burr sleeve for nonrotatably holding a dental treatment tool, upper and lower ball bearings for rotatably supporting said burr sleeve, each of said upper and lower ball bearings having an inner ring, an outer ring, and a plurality of balls between said inner and outer rings, a rotor disposed between said upper and lower ball bearings and rotated by compressed air for rotatively driving said burr sleeve, said rotor defining a rotation space within the head housing, a rolling bearing cage for supporting said plurality of balls at regular intervals in each of said upper and lower ball bearings, each said cage having a side facing the rotor, and a baffle member disposed facing said side of each cage to define a first gap between said baffle member and its cage.

2. The dental handpiece of claim 1 further comprising a dust preventive member projecting from and rotating with the burr sleeve, wherein said dust preventive member has an outer surface defining a second gap having two ends, one of said two ends of the second gap communicating with one of the upper and lower ball bearings, the other of said two ends of the second gap being opened to outside the head housing.

3. The dental handpiece of claim 1 further comprising an air discharge passage having a port opened to the rotation space of the rotor, said passage communicating with the rotation space at said port to discharge the compressed air out of the head housing, wherein an axial length of the rotor is substantially equal to a diameter of said port of the air discharge passage measured in an axial direction of the rotor, and wherein said baffle member defines a third gap between the baffle member and the rotor.

4. The dental handpiece of claim 1 wherein each said baffle member is secured to and rotates with the burr sleeve.

5. The dental handpiece of claim 1 wherein each said baffle member is secured to the head housing.

6. The dental handpiece of claim 1 wherein each said baffle member is in a form of an annular disk.

7. The dental handpiece of claim 6 wherein said annular disk has an annular step.

* * * * *